United States Patent
Guo (10) Patent No.: US 11,339,372 B2
(45) Date of Patent: May 24, 2022

(54) SERUM-FREE MEDIUM INDUCING DIFFERENTIATION OF UMBILICAL CORD MESENCHYMAL STEM CELL INTO INSULIN-SECRETION-LIKE CELL AND PREPARATION METHOD AND USE THEREOF

(71) Applicants: Cheng Li, Beijing (CN); Lei Guo, Beijing (CN); SCLNOW BIOTECHNOLOGY CO., LTD, Beijing (CN)

(72) Inventor: Lei Guo, Beijing (CN)

(73) Assignees: Cheng Li, Beijing (CN); Lei Guo, Beijing (CN); SCLNOW BIOTECHNOLOGY CO., LTD., Beijing (CN)

(*) Notice: Subject to any disclaimer, the term of this patent is extended or adjusted under 35 U.S.C. 154(b) by 281 days.

(21) Appl. No.: 16/346,762

(22) PCT Filed: May 3, 2017

(86) PCT No.: PCT/CN2017/082791
§ 371 (c)(1),
(2) Date: May 1, 2019

(87) PCT Pub. No.: WO2018/086319
PCT Pub. Date: May 17, 2018

(65) Prior Publication Data
US 2019/0264179 A1 Aug. 29, 2019

(30) Foreign Application Priority Data
Nov. 8, 2016 (CN) .......................... 201610979689.6
Nov. 8, 2016 (CN) .......................... 201610980017.7

(51) Int. Cl.
*C12N 5/0775* (2010.01)
*C12N 5/071* (2010.01)

(52) U.S. Cl.
CPC ......... *C12N 5/0668* (2013.01); *C12N 5/0665* (2013.01); *C12N 5/0676* (2013.01); *C12N 2500/25* (2013.01); *C12N 2500/30* (2013.01); *C12N 2500/32* (2013.01); *C12N 2500/34* (2013.01); *C12N 2500/90* (2013.01); *C12N 2500/99* (2013.01); *C12N 2501/11* (2013.01); *C12N 2501/115* (2013.01); *C12N 2501/12* (2013.01); *C12N 2501/345* (2013.01); *C12N 2506/1369* (2013.01); *C12N 2506/1392* (2013.01)

(58) Field of Classification Search
CPC .. C12N 5/0668; C12N 5/0665; C12N 5/0676; C12N 2506/1369; C12N 2500/99; C12N 2500/25; C12N 2500/30; C12N 2500/32; C12N 2500/34; C12N 2500/90; C12N 2501/11; C12N 2501/115; C12N 2501/12; C12N 2501/345; C12N 2506/1392
See application file for complete search history.

(56) References Cited

FOREIGN PATENT DOCUMENTS

CN 102618491 A * 8/2012
WO 2007046775 A1 4/2007

OTHER PUBLICATIONS

Chandra V, Swetha G, Muthyala S, Jaiswal AK, Bellare JR, Nair PD, Bhonde RR. Islet-like cell aggregates generated from human adipose tissue derived stem cells ameliorate experimental diabetes in mice. PLoS One. 2011;6(6):e20615. (Year: 2011).*
Zanini C, Bruno S, Mandili G, Baci D, Cerutti F, Cenacchi G, Izzi L, Camussi G, Forni M. Differentiation of mesenchymal stem cells derived from pancreatic islets and bone marrow into islet-like cell phenotype. PLoS One. 2011;6(12):e28175. (Year: 2011).*
Dave S. Mesenchymal stem cells derived in vitro transdifferentiated insulin-producing cells: A new approach to treat type 1 diabetes. Adv Biomed Res. Dec. 31, 2014;3:266. (Year: 2014).*
Ling et al. Effect of heparin on the biological properties and molecular signature of human mesenchymal stem cells. Gene. Jan. 15, 2016;576 (1 Pt 2): 292-303 (Year: 2016).*
Nonessential amino acids. (Mar. 30, 2013). What are nonessential amino acids and why are they added to some cell culture media? ATCC. https://www.atcc.org/support/faqs/a882a/Nonessential+amino+acids+NEAA-85.aspx. (Year: 2013).*
Subculturing Adherent cells. (Nov. 10, 2015). Subculturing Adherent cells. ThermoFisher, https://www.thermofisher.com/us/en/home/references/gibco-cell-culture-basics/cell-culture-protocols/subculturing-adherent-cells.html (Year: 2015).*
Sibov TT, Severino P, Marti LC, Pavon LF, Oliveira DM, Tobo PR, Campos AH, Paes AT, Amaro E Jr, F Gamarra L, Moreira-Filho CA. Mesenchymal stem cells from umbilical cord blood: parameters for isolation, characterization and adipogenic differentiation. Cytotechnology. Oct. 2012;64(5):511-21 (Year: 2012).*
English Translation of CN 102618491 A (5 pages).
English Translation of CN 105670986 A (2 pages).
International Search Report dated Aug. 8, 2017 for corresponding PCT Application No. PCT/CN2017/082791, with English Translation (6 pages).

* cited by examiner

Primary Examiner — Teresa E Knight
(74) Attorney, Agent, or Firm — Lewis Roca Rothgerber Christie LLP (57) ABSTRACT

Provided is a new type serum-free medium. The medium comprises: DMEM with high glucose (the content of glucose being 4.5 g/L), B27, recombinant human basic fibrolast growth factor (b-FGF), nicotinamide, N-2, vinblastine III (conophylline), non-essential amino acid (NEAA), heparin, epidermal growth factor (EGF), hepatocyte growth factor (HGF), a serum replacement (SR), an insulin-transferrin-selenium complex (ITS), and pentagastrin. Inducing differentiation of mesenchymal stem cells into insulin-secretion-like cells can be achieved in six days in one step using the medium.

11 Claims, 8 Drawing Sheets

SERUM-FREE MEDIUM INDUCING DIFFERENTIATION OF UMBILICAL CORD MESENCHYMAL STEM CELL INTO INSULIN-SECRETION-LIKE CELL AND PREPARATION METHOD AND USE THEREOF

CROSS-REFERENCE TO RELATED APPLICATION(S)

This application is a National Phase Patent Application of International Patent Application Number PCT/CN2017/082791, filed on May 3, 2017, which claims priority of Chinese Patent Application Nos. 201610980017.7, filed Nov. 8, 2016 and 201610979689.6, filed Nov. 8, 2016. The entire contents of all of which are incorporated herein by reference.

TECHNICAL FIELD

The present invention relates to the field of stem cell research. Particularly, the present invention relates to a novel, high efficient serum-free culture medium suitable for inducing mesenchymal stem cells to differentiate into insulin-secreting like cells and preparation method and application therefor.

BACKGROUND OF THE INVENTION

Diabetes, which has become an epidemic worldwide in the 21st century, is the third most serious non-communicable disease that threatens human health after tumor and vascular disease. It is characterized by high mortality and disability rates, and high medical costs. So far China has people suffering from diabetes in a number of 114 million, which now ranks first in the world and accounts for about one-third of the total number of diabetes patients worldwide. Therefore, diabetes has become a serious public health challenge for the world, especially for China.

With the rise and development of human organ transplantation technology from the middle of the 20th century, pancreas transplantation has been introduced into the medical field to serve as a therapy for diabetes. However, there are still many problems, such as limited number of organs available for transplantation, daunting cost needed for organ transplantation, and strong immune rejection caused by organ transplantation, that are troubling doctors and patients all the time.

In recent years, the rapid development of stem cell theory and technology brings new hope for treatment of patients with diabetes. In particular, the confirmation of the transdifferentiation ability of adult stem cells (that is, adult stem cells can horizontally differentiate into specific cells and tissues under the action of a certain microenvironment) provides an alternative source of cells for treating diabetes with cell transplantation. Studies have shown that bone marrow mesenchymal cells, adult adipocytes, and cord blood stem cells can differentiate into islet-like cells under specific conditions. Those islet-like cells secrete insulin in vitro and are expected to be another source of cells for treating diabetes with cell transplantation.

Umbilical cord mesenchymal stem cells, which originate from mesoderm, have subpotential differentiation potential and can differentiate into tissue cells of the three germ layers under both in vitro and in vivo specific microenvironment conditions. Compared with other adult stem cells, umbilical cord mesenchymal stem cells are easy to obtain and have abundant sources. They are derived from umbilical cord tissue, which is usually regarded as medical waste, and no moral ethical problem is needed to consider. In addition, umbilical cord mesenchymal stem cells have the advantages of rapid proliferation rate in vitro, lower immunogenicity, and less exogenous pollution, and thus have more research value.

SUMMARY OF THE INVENTION

The inventors of the present invention have found in research a novel, high efficient serum-free culture medium suitable for inducing mesenchymal stem cells to differentiate into insulin-secreting like cells, by which umbilical cord mesenchymal stem cells can differentiate into insulin-secreting like cells after being induced for 6-7 days under in vitro serum-free conditions.

One purpose of the present invention is to provide a serum-free medium for inducing umbilical cord mesenchymal stem cells to differentiate into insulin-secreting like cells, by which the umbilical cord mesenchymal stem cells can differentiate into insulin-secreting like cells rapidly within 6 days.

Another purpose of the present invention is to provide a method for preparing the serum-free medium.

Yet another purpose of the present invention is to provide a method for inducing the umbilical cord mesenchymal stem cells to differentiate using the serum-free medium.

Still another purpose of the present invention is to provide a use of the serum-free medium.

Technical solutions provided by the present invention are as follows.

In one aspect, the present invention provides a serum-free medium for inducing umbilical cord mesenchymal stem cells (UC-MSCs) to differentiate into insulin-secreting like cells, said serum-free medium comprising DMEM (High Glucose), serum replacement (SR), B27 serum-free supplement, insulin-transferrin-selenium (ITS), non-essential amino acids (NEAA), N-2 serum-free supplement, and heparin, conophylline, nicotinamide, and recombinant human basic fibroblast growth factor (b-FGF), epidermal growth factor (EGF), hepatocyte growth factor (HGF) and pentagastrin.

Preferably, in 100 parts by volume, the serum-free medium comprises 85-95 parts by volume of DMEM (High Glucose, with 4.5 g/L glucose), 5-8 parts by volume of serum replacement (SR), 1-4 parts by volume of B27 serum-free supplement (50×), 1-1.5 parts by volume of insulin-transferrin-selenium (ITS), 0.5-2 parts by volume of aqueous solution of non-essential amino acids (NEAA), 0.5-2 parts by volume of N-2 serum-free supplement (100×), and comprises in the serum-free medium heparin in a final concentration of 0.5-2 μg/ml, conophylline in a final concentration of 50-200 ng/ml, nicotinamide in a final concentration of 5-20 mmol/L, and recombinant human basic fibroblast growth factor (b-FGF), epidermal growth factor (EGF), hepatocyte growth factor (HGF) and pentagastrin each in a final concentration of 5-20 ng/ml.

More preferably, in 100 parts by volume, the serum-free medium comprises 89 parts by volume of DMEM (High Glucose, with 4.5 g/L glucose), 5 parts by volume of serum replacement (SR), 2 parts by volume of B27 serum-free supplement (50×), 1 part by volume of Insulin-Transferrin-Selenium (ITS), 1 part by volume of aqueous solution of non-essential amino acids (NEAA), 1 part by volume of N-2 serum-free supplement (100×), and comprises in the serum-free medium heparin in a final concentration of 1 μg/ml, conophylline in a final concentration of 100 ng/ml, nicotinamide in a final concentration of 10 mmol/L, and recombinant human basic fibroblast growth factor (b-FGF), epidermal growth factor (EGF), hepatocyte growth factor (HGF) and pentagastrin each in a final concentration of 10 ng/ml.

The aqueous solution of non-essential amino acids comprises glycine, alanine, L-aspartamide, L-aspartic acid, glutamic acid, proline and serine each in a concentration of 8-12 mM.

According to specific embodiments of the present invention, the aqueous solution of non-essential amino acids can be a product available from Gibco under catalog number 11140.

According to specific embodiments of the present invention, the serum replacement can be KnockOut™ Serum Replacement, a product available from Gibco under catalog number 10828-010.

According to specific embodiments of the present invention, the B27 serum-free supplement (50×) can be a product available from Gibco under catalog number 17504044.

According to specific embodiments of the present invention, the insulin-transferrin-selenium (ITS) can be a product available from Sigma under catalog number 13146.

According to specific embodiments of the present invention, the N-2 serum-free supplement (100×) can be a product available from Gibco under catalog number 17502048.

In case the total volume of the serum-free medium is 100 mL, its composition can be as shown in Table 1 below.

TABLE 1

| Ingredient | Amount |
| --- | --- |
| DMEM medium (High Glucose, with 4.5 g/L glucose) | 85-95 ml |
| SR | 5-8 ml |
| B27 (50X) | 1-4 ml |
| ITS | 1-1.5 ml |
| N-2 (100X) | 0.5-2 ml |
| NEAA | 0.5-2 ml |
| Heparin | 50-200 µg |
| Conophylline (100 µg/ml) | 5-20 µg |
| Nicotinamide | 0.5-2 mmol |
| b-FGF (1 µg/ml) | 0.5-2 µg |
| EGF | 0.5-2 µg |
| HGF | 0.5-2 µg |
| Pentagastrin | 0.5-2 µg |

More preferably, the composition of the serum-free medium can be as shown in Table 2 below.

TABLE 2

| Ingredient | Amount |
| --- | --- |
| DMEM medium (High Glucose, with 4.5 g/L glucose) | 89 ml |
| SR | 5 ml |
| B27 (50X) | 2 ml |
| ITS | 1 ml |
| N-2 (100X) | 1 ml |
| NEAA | 1 ml |
| Heparin | 100 µg |
| Conophylline (100 µg/ml) | 10 µg |
| Nicotinamide | 1 mmol |
| b-FGF (1 µg/ml) | 1 µg |
| EGF | 1 µg |
| HGF | 1 µg |
| Pentagastrin | 1 µg |

For the serum-free medium of the present invention, the umbilical cord mesenchymal stem cells are umbilical cord mesenchymal stem cells of human origin (hUC-MSCs), preferably human umbilical cord mesenchymal stem cells isolated from a fresh umbilical cord tissue of a healthy newborn delivered naturally or by cesarean section.

In another aspect, the present invention provides a method for preparing the above serum-free medium, the method including: mixing the ingredients well.

In yet another aspect, the present invention provides a method for inducing umbilical cord mesenchymal stem cells to differentiate into insulin-secreting like cells, the method including: culturing the umbilical cord mesenchymal stem cells with the serum-free medium of the present invention.

Preferably, the umbilical cord mesenchymal stem cells are umbilical cord mesenchymal stem cells of human origin, more preferably human umbilical cord mesenchymal stem cells isolated from a fresh umbilical cord tissue of a healthy newborn delivered naturally or by cesarean section.

Preferably, the method includes the following steps:

(1) inoculating umbilical cord mesenchymal stem cells in the serum-free medium at a density of $2\text{-}6 \times 10^4$ cells/cm$^2$ and culturing the cells at 37° C., 5% $CO_2$, for example, culturing the cells in a constant temperature incubator at 37° C. with a $CO_2$ concentration of 5%;

(2) centrifuging the cell culture of step (1) at 300-800 rpm for 4 min every 2-3 days, removing the medium, and replacing with fresh serum-free medium; for example, pipetting cell suspension in the medium into a centrifuge tube slowly, centrifuging at 300-800 rpm for 4 min at a low speed, then removing the medium, and replacing with fresh serum-free medium of the present invention, with the medium renewed every 2-3 days;

(3) culturing for 6-7 days, and harvesting cells;

(4) detecting the cells harvested in step (3) for effect of differentiation induction.

Wherein, the step (4) comprises detecting one or more (preferably, e.g., all) items selected from the group consisting of:

Amount of insulin released per cell; expression of insulin release-related genes PDX-1, INSULIN and NGN-3; presence of cell nuclear protein PDX-1 and cytosol protein Insulin; positive expression rates of specific markers PDX-1, NKX6.1 and Insulin of insulin-secreting like cells.

More preferably, the method includes the following steps:

(1) inoculating umbilical cord mesenchymal stem cells in the serum-free medium in a ultra-low attachment six well plate at a density of $5 \times 10^4$ cells/cm$^2$ and culturing the cells at 37° C., 5% $CO_2$, for example, culturing the cells in a constant temperature incubator at 37° C. with a $CO_2$ concentration of 5%;

(2) centrifuging the cell culture of step (1) at 500 rpm for 4 min every 2 days, removing the medium, and replacing with fresh serum-free medium; for example, pipetting cell suspension in the medium into a centrifuge tube slowly, centrifuging at 500 rpm for 4 min at a low speed, then removing the medium, and replacing with fresh serum-free medium of the present invention, with the serum-free medium renewed every 2 days;

(3) culturing for 6-7 days, and harvesting cells;

(4) detecting the cells harvested in step (3) for effect of differentiation induction.

In step (1), the umbilical cord mesenchymal stem cells (UC-MSCs) are preferably umbilical cord mesenchymal stem cells of human origin (hUC-MSCs), more preferably human umbilical cord mesenchymal stem cells isolated from a fresh umbilical cord tissue of a healthy newborn delivered naturally or by cesarean section.

In still another aspect, the present invention provides a use of the serum-free medium in the preparation of an agent for stem cell culture.

The stem cells are isolated from tissue or organ of a mammal, such as human, which is one or more selected from the group consisting of bone marrow, umbilical cord and fat; preferably, the stem cells are umbilical cord mesenchymal stem cells of mammalian origin; more preferably, the stem cells are umbilical cord mesenchymal stem cells of human origin; further preferably, the stem cells are human umbilical cord mesenchymal stem cells isolated from a fresh umbilical cord tissue of a healthy newborn delivered naturally or by cesarean section.

Researches by the inventors have found that, the novel serum-free medium for inducing mesenchymal stem cells to differentiate into insulin-secreting like cells provided by the present invention contains no serum ingredients, thereby avoiding instable cell growth during the culture resulted from batch difference of serum, and excluding the possibility of transmitting xenogeneic pathogens. Meanwhile, the present serum-free medium can induce the mesenchymal stem cells to differentiate into insulin-secreting like cells rapidly (only 6 days are needed), which provides an efficient solution for in vitro culture of animal cells.

BRIEF DESCRIPTION OF THE DRAWINGS

Hereinafter, embodiments of the present invention will be described with reference to the accompanying drawings in detail, in which:

In FIG. 7, M represents nucleic acid molecular weight marker, 1 represents internal reference gene GAPDH, 2 represents PDX-1, 3 represents INSULIN, and 4 represents NGN-3.

In FIG. 9, the negative group is cells before induction, the induction group is cells after induction for 6 days, and the positive control group is insulinoma cells.

DETAILED DESCRIPTION OF PREFERRED EMBODIMENTS

The present invention will be further described in detail in combination with the specific embodiments hereinafter. It will be appreciated by those skilled in the art that the embodiments provided are only used to illustrate the present invention, rather than limiting the scope of the present invention in any way.

Experimental methods in the following examples, if no any other special instruction is provided, are all conventional methods. Medicinal materials and agents used in the following examples, if no any other special instruction is provided, are conventional products that can be commercially available.

NEAA used in following examples is an aqueous solution of non-essential amino acids comprising glycine, alanine, L-aspartamide, L-aspartic acid, glutamic acid, proline and serine each in a concentration of 10 mM.

Example 1: Screening for the Composition of the Medium

Basal culture medium: DMEM (with 4.5 g/L glucose)+5% SR+1% NEAA+2% B27 (50×)+1% N-2 (100×)+10 ng/ml HGF+10 ng/ml EGF+10 ng/ml b-FGF+10 mmol/L Nicotinamide.

Ingredients to be screened: 100 ng/ml conophylline, 1 part by volume of ITS, heparin in a final concentration of 1 μg/ml, and betacellulin, Exendi-4, insulin-like growth factor 1 (IGF-1) and pentagastrin each in a final concentration of 10 ng/ml, added to the basal culture medium. Ingredients comprised in each group of medium to be tested were shown in Table 3.

TABLE 3

| | Basal culture medium | Conophylline 100 ng/ml | Pentagastrin 10 ng/ml | Heparin 1 μg/ml | ITS 1% | betacellulin 10 ng/ml | Exendi-4 10 ng/ml | IGF-1 10 ng/ml |
|---|---|---|---|---|---|---|---|---|
| Group 1 | ✓ | | | | | | | |
| Group 2 | ✓ | ✓ | | | | | | |
| Group 3 | ✓ | ✓ | ✓ | | | | | |
| Group 4 | ✓ | ✓ | ✓ | ✓ | | | | |
| Group 5 | ✓ | ✓ | ✓ | ✓ | ✓ | | | |
| Group 6 | ✓ | ✓ | ✓ | ✓ | ✓ | ✓ | | |
| Group 7 | ✓ | ✓ | ✓ | ✓ | ✓ | ✓ | ✓ | |
| Group 8 | ✓ | ✓ | ✓ | ✓ | ✓ | ✓ | ✓ | ✓ |

In a biosafety cabinet, the third generation hUC-MSCs isolated from Wharton's jelly tissue of umbilical cord of a newborn delivered naturally were inoculated into a ultra-low attachment six well plate at a density of 5×10$^4$ cells/cm$^2$, then 2 ml of one of the media to be tested as shown in Table 3 was added in one well and the growth of the cells and the amount of cell clusters formed by the cells were observed.

Figure 1:
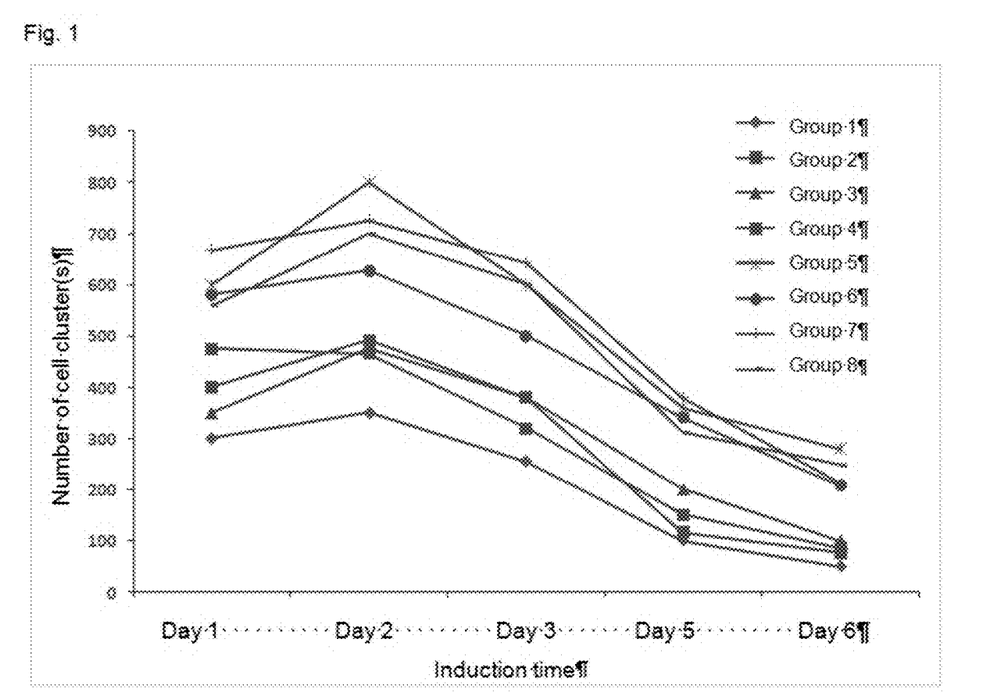
FIG. 1 shows a trend chart of the number of cell clusters (>50 μm in diameter) over culture time during screening for the composition of the medium.

Results: a small number of cell clusters formed in the medium of group 1; in the media of groups 2, 3 and 4 which had conophylline, pentagastrin and heparin added in respectively, the cell clusters showed an increased number but loose structures; the medium of group 5 had the largest number of cell clusters whose maturity was the best also; while in the media of groups 6, 7 and 9 which had betacellulin, Exendi-4 and insulin-like growth factor 1 added in respectively, little effect on the increase in the number of cell clusters was shown by those three ingredients. The results are shown in FIG. 1.

Example 2: Screening for the Content of Ingredient (Conophylline) in the Medium Media to be tested: 89 parts by volume of DMEM (High Glucose, with 4.5 g/L glucose), 5 parts by volume of serum replacement (SR), 2 parts by volume of B27 (50×), 1 part by volume of ITS, 1 part by volume of non-essential amino acids (NEAA), 1 part by volume of N-2 (100×), and heparin in a final concentration of 1 μg/ml, 10 mmol/L nicotinamide, and recombinant human basic fibroblast growth factor (b-FGF), epidermal growth factor (EGF), hepatocyte growth factor (HGF) and pentagastrin each in a final concentration of 10 ng/ml, and conophylline with a concentration of 1, 10, 50, 100, 200, and 300 ng/ml respectively.

Human umbilical cord mesenchymal stem cells were induced to differentiate through being cultured in the above media comprising different concentrations of conophylline respectively.

Results: in the two groups of media to be tested which comprise 1 ng/ml and 10 ng/ml conophylline respectively, free cells were found to attach to the edge of cell clusters, and the cell clusters became loose with the prolonging culture time, indicating that the maturity of the cell clusters was insufficient; in the three groups of media to be tested which comprise 50 ng/ml, 100 ng/ml and 200 ng/ml conophylline respectively, cell clusters were compact and grew gradually, indicating that the cell clusters were in a good proliferation; while in the group of medium comprising 300 ng/ml conophylline, the color of the cell clusters was deeper, but the cells at the edge of the cell clusters had changed morphology, indicating that the differentiated cells had undergone an undirected differentiation.

Example 3: Screening for the Content of Ingredient (Pentagastrin) in the Medium Media to be tested: 89 parts by volume of DMEM (High Glucose, with 4.5 g/L glucose), 5 parts by volume of serum replacement (SR), 2 parts by volume of B27 (50×), 1 part by volume of ITS, 1 part by volume of non-essential amino acids (NEAA), heparin in a final concentration of 1 μg/ml, 1 part by volume of N-2 (100×), 100 ng/ml conophylline, 10 mmol/L nicotinamide, recombinant human basic fibroblast growth factor (b-FGF), epidermal growth factor (EGF), and hepatocyte growth factor (HGF) each in a final concentration of 10 ng/ml, and pentagastrin with a concentration of 1, 2, 5, 10, 20, 30, and 50 ng/ml respectively.

Human umbilical cord mesenchymal stem cells were induced to differentiate through being cultured in the above media comprising different concentrations of pentagastrin respectively, and subsequently the cells obtained from the groups were compared using a glucose stimulation experiment which detects the amount of insulin released per cell (1×10$^4$ cells in this case). The glucose stimulation experiment was conducted as follows: cell clusters were collected when the cells had been cultured for 6 days, added into a stimulating liquid, 2 ml DMEM with 25 mM/L glucose, and then were blown gently and mixed well; and supernatant was collected after stimulation for 2 hours at 37° C., detected with an insulin ELISA kit, and OD450 value was read finally.

Figure 2:
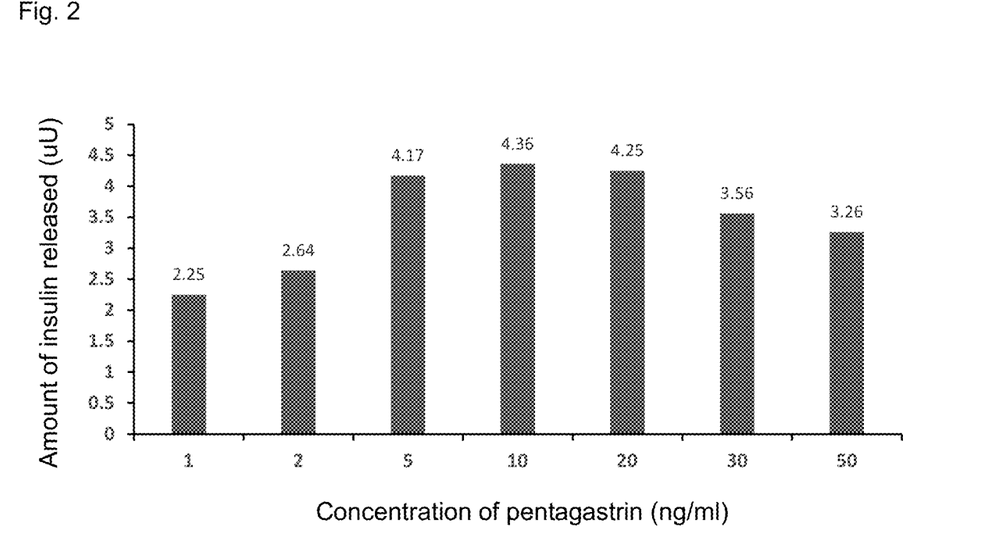
FIG. 2 shows a comparison of amounts of insulin released per cell induced in media with different concentrations of pentagastrin.

Results: the cells differentiated in the media comprising pentagastrin concentrations of 5, 10, and 20 ng/ml respectively had higher amounts of insulin released per cell. The results are shown in FIG. 2.

Example 4: Screening for the Content of Ingredient (ITS) in the Medium

Media to be tested: 89 parts by volume of DMEM (High Glucose, with 4.5 g/L glucose), 5 parts by volume of serum replacement (SR), 2 parts by volume of B27 (50×), 1 part by volume of ITS, 1 part by volume of non-essential amino acids (NEAA), heparin in a final concentration of 1 μg/ml, 1 part by volume of N-2 (100×), 100 ng/ml conophylline, 10 mmol/L nicotinamide, and recombinant human basic fibroblast growth factor (b-FGF), epidermal growth factor (EGF), hepatocyte growth factor (HGF) and pentagastrin each in a final concentration of 10 ng/ml, and ITS with a concentration of 0.2, 0.5, 0.8, 1.0, 1.2, 1.5, and 2.0 ng/ml respectively.

Human umbilical cord mesenchymal stem cells were induced to differentiate through being cultured in the above media comprising different concentrations of ITS respectively.

Figure 3:
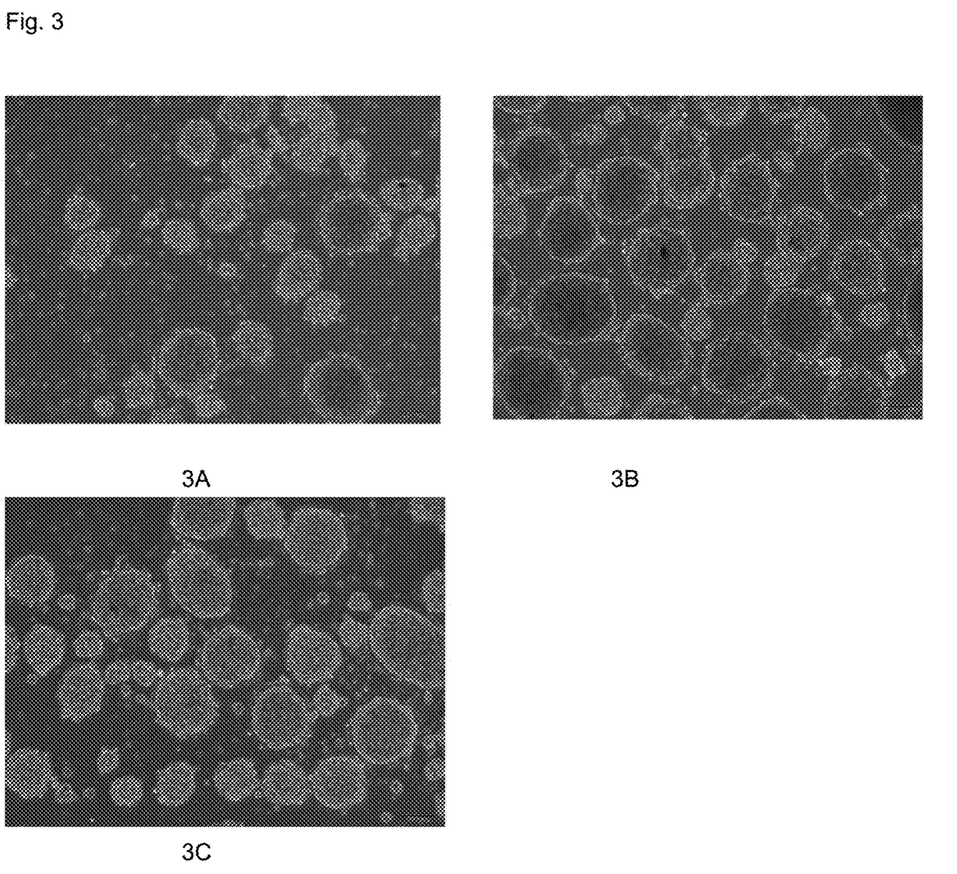
FIG. 3 shows a comparison of cellular morphology of cells induced in media with different concentrations of ITS, in which panel 3A shows cellular morphology of cells induced for 6 days in medium with 0.5 parts by volume of ITS; panel 3B shows cellular morphology of cells induced for 6 days in medium with 1.0 part by volume of ITS; and panel 3C shows cellular morphology of cells induced for 6 days in medium with 2.0 parts by volume of ITS.

Results: in the media comprising 0.2, 0.5, and 0.8 ng/ml ITS respectively, the cells were loose and even died, cell clusters formed were uneven and had smaller diameters, and many dead cells were found at the bottom of the plate; in the media comprising 1.0, 1.2 and 1.5 ng/ml ITS respectively, the cells tightly clustered; while in the medium comprising 2.0 ng/ml ITS, cell clusters formed were compact, but dead cells began to appear and showed an gradually increased number. The results are shown in FIG. 3.

Example 5: Screening for Induction Time

Preparation of the serum-free medium for inducing differentiation:

Composition: 89 parts by volume of DMEM (High Glucose, with 4.5 g/L glucose), 5 parts by volume of serum replacement (SR), 2 parts by volume of B27 (50×), 1 part by volume of ITS, 1 part by volume of non-essential amino acids (NEAA), 1 part by volume of N-2 (100×), heparin in a final concentration of 1 μg/ml, 100 ng/ml conophylline, 10 mmol/L nicotinamide, and recombinant human basic fibroblast growth factor (b-FGF), epidermal growth factor (EGF), hepatocyte growth factor (HGF) and pentagastrin each in a final concentration of 10 ng/ml.

The above ingredients were mixed with each other well to prepare the medium.

Culture of Cells:

In a biosafety cabinet, the third generation hUC-MSCs isolated from Wharton's jelly tissue of umbilical cord of a newborn delivered naturally were inoculated into a ultra-low attachment six well plate at a density of $5 \times 10^4$ cells/cm$^2$, then the plate was transferred to a constant temperature incubator at 37° C., 5% $CO_2$ after 2 ml of the medium of the present invention was added in each well. Cell suspension in the medium was pipetted into a centrifuge tube slowly, centrifuged at 500 rpm for 4 min at a low speed, then the medium was removed and replaced with fresh serum-free medium of the present invention, with the serum-free medium renewed every 2 days. The amount of cell clusters formed by the cells was observed and counted during continuous induction for 10 days.

Figure 4:
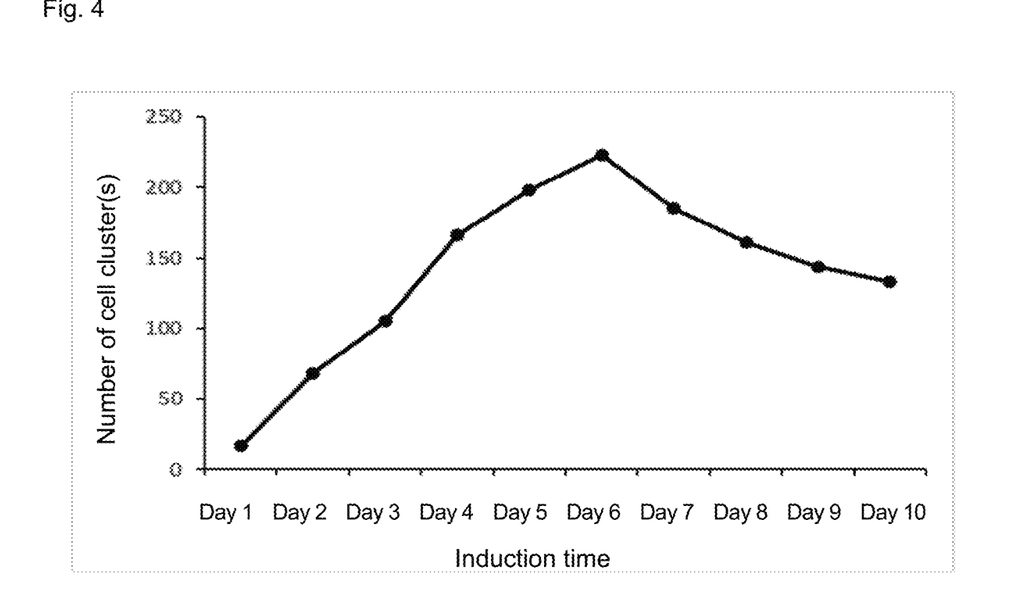
FIG. 4 shows a trend chart of the number of cell clusters (>100 μm in diameter) over culture time during inducing umbilical cord mesenchymal stem cells to differentiate into insulin-secreting like cells using the medium of the present invention (within 10 days).

Results: the number of cell clusters gradually increased in the first six days since the induction started, reached the maximum (223) on the sixth day, and gradually decreased after the sixth day. The results are shown in FIG. 4.

Example 6: Preparation and Application of the Serum-Free Medium

Preparation of the serum-free medium for inducing differentiation:

Composition: 89 parts by volume of DMEM (High Glucose, with 4.5 g/L glucose), 5 parts by volume of serum replacement (SR), 2 parts by volume of B27 (50×), 1 part by volume of ITS, 1 part by volume of non-essential amino acids (NEAA), 1 part by volume of N-2 (100×), heparin in a final concentration of 1 μg/ml, 100 ng/ml conophylline, 10 mmol/L nicotinamide, and recombinant human basic fibroblast growth factor (b-FGF), epidermal growth factor (EGF), hepatocyte growth factor (HGF) and pentagastrin each in a final concentration of 10 ng/ml.

The above ingredients were mixed with each other well to prepare the medium. The culture of cells was conducted according to the method as described in Example 5, and then cellular morphologic change of cell clusters was observed for 6 days continuously.

Figure 5:
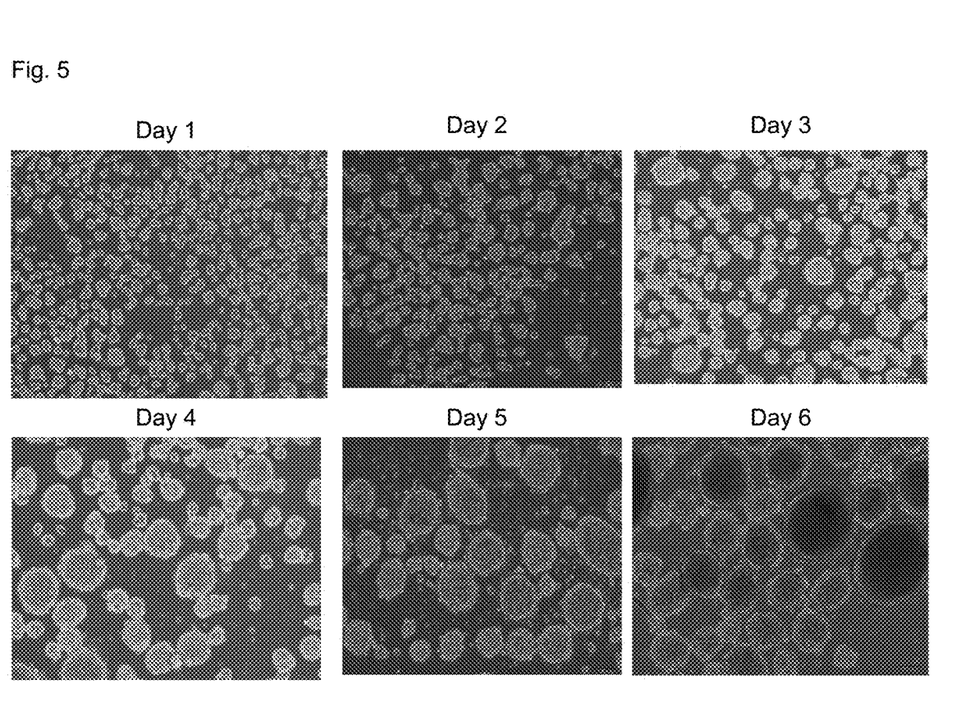
FIG. 5 shows cellular morphologic changes of cell clusters during inducing umbilical cord mesenchymal stem cells to differentiate into insulin-secreting like cells using the medium of the present invention (within 6 days).

Results: after the first day of the induction, the cells agglomerated and formed small cell clusters which were in a large number and had high light transmission; with the culture time prolonged, the small cell clusters gradually converged into large cell clusters, the number of small cell clusters decreased, and the number of large cell clusters gradually increased, and as the diameter of the cell clusters became larger, the light transmission of the cell clusters gradually decreased; and after 6 days of the culture, large cell clusters (mature cell clusters) occupied most of the field of view. The results are shown in FIG. 5.

Example 7: Analysis of Specific Markers on the Surface of Insulin-Secreting Like Cells by Flow Cytometry After differentiation induction for 6 days, cell clusters in Example 6 were collected in a centrifuge tube, and then centrifuged at 500 rpm for 4 minutes at 4° C. The supernatant was discarded, the cell clusters remained were collected, and 0.25% trypsin was added in while gently pipetting and mixing for 20 min. The digestion was stopped by adding fresh medium when the structure of the cell clusters was loose and no suspended cell cluster could be seen by naked eyes, and then the tube was centrifuged at 1200 rpm for 6 minutes. The supernatant was discarded and the cells were collected and washed twice with PBS. The cells were then transferred to tubes for flow cytometry in an amount of $1 \times 10^5$ cells per tube, and 500 μL of 4% paraformaldehyde was added into each tube for immobilization for 30 min at room temperature, and then the tubes were centrifuged at 1200 rpm for 6 minutes. The supernatant was discarded, the cells were collected and 5 μL of each of antibodies against PDX-1, NKX6.1, Insulin, and IgG1-PE (isotype control) was added into one of the tubes respectively. The cells were mixed well and incubated in dark for 30 minutes at 4° C., washed once with PBS, centrifuged and the supernatant was discarded. The collected cells were resuspended by addition of 500 μL PBS, and then detected on a Flow Cytometer (Flow Cytometer XL, Beckman). $1 \times 10^4$ cells were collected from each sample.

Figure 6:
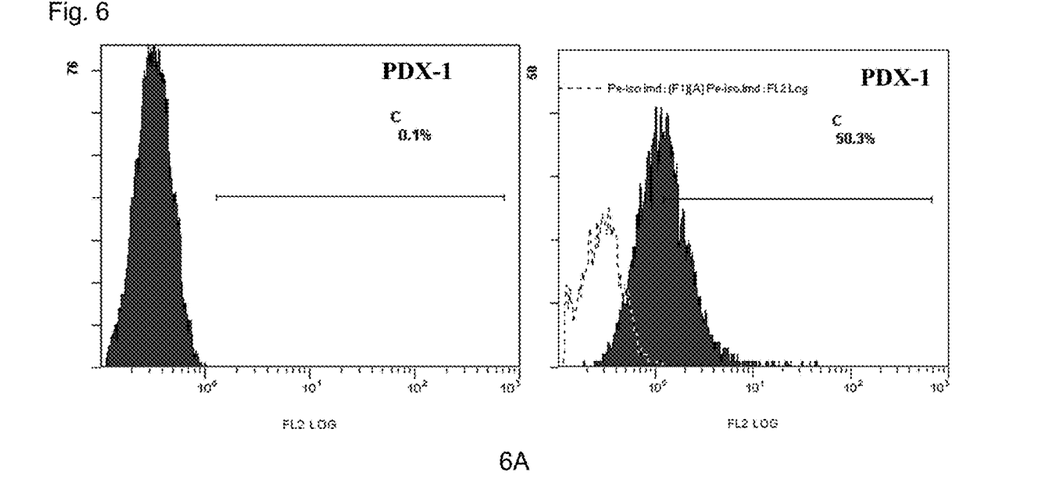
FIG. 6 shows analysis results of specific molecules on the surface of insulin-secreting like cells obtained by inducing with the medium of the present invention by flow cytometry, in which panel 6A shows changes of PDX-1 before and after the induction; panel 6B shows changes of NKx6.1 before and after the induction; panel 6C shows changes of insulin before and after the induction, with panels on the left showing the results before the induction and panels on the right the results after induction for 6 days.

Results: the mesenchymal stem cells expressed specific markers of insulin-secreting like cells after being induced for 6 days, in which the positive expression rate of PDX-1 detected by Flow Cytometer was 51.4%, the positive expression rate of NKx6.1 was 15.36%, and the positive expression rate of insulin was 24.03%. The cells before induction did not express those specific markers. The results are shown in FIG. 6.

Example 8: RT-PCR Analysis of Insulin-Secreting Like Cells Specific Genes

After differentiation induction for 6 days, cell clusters in Example 6 were collected in a centrifuge tube, and then RNAs were extracted according to the instruction of Total RNA Kit I (R6834-01, OMRGA). The extracted RNAs were reversely transcribed to obtain cDNA samples using a reverse transcription kit (RR014A, TAKARA), and then the cDNA samples were subjected to PCR amplification. After agarose gel electrophoresis, a gel imager was used for observation.

Figure 7:
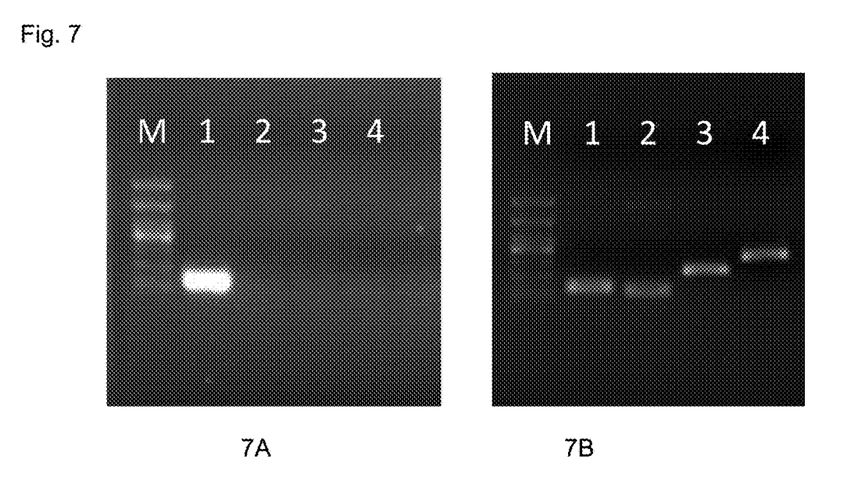
FIG. 7 shows RT-PCR analysis results at transcription level of specific genes of insulin-secreting like cells obtained by inducing umbilical cord mesenchymal stem cells with the medium of the present invention, in which panel 7A shows the results before the induction and panel 7B shows the results after induction for 6 days.

Results: the cells expressed insulin-secreting like cells specific genes after being induced, and bands of PDX-1, INSULIN and NGN-3 with varying brightness could be seen. The results are shown in FIG. 7.

Example 9: Analysis of hUC-MSCs Specific Proteins by Immunofluorescence Staining After differentiation induction for 6 days, cell clusters in Example 6 were collected in a centrifuge tube, immobilized for 15 min with 4% paraformaldehyde, and then treated with 0.25% TritonX-100 for 20 min. Diluted red mouse anti-human antibody (anti-Insulin antibody) was added in after the cells were blocked with goat serum, and then incubated with the cells in dark overnight at 4° C. Afterwards, nuclear protein PDX-1 was stained, the cells were incubated in dark overnight at 4° C., and then observed under a fluorescence microscope.

Figure 8:
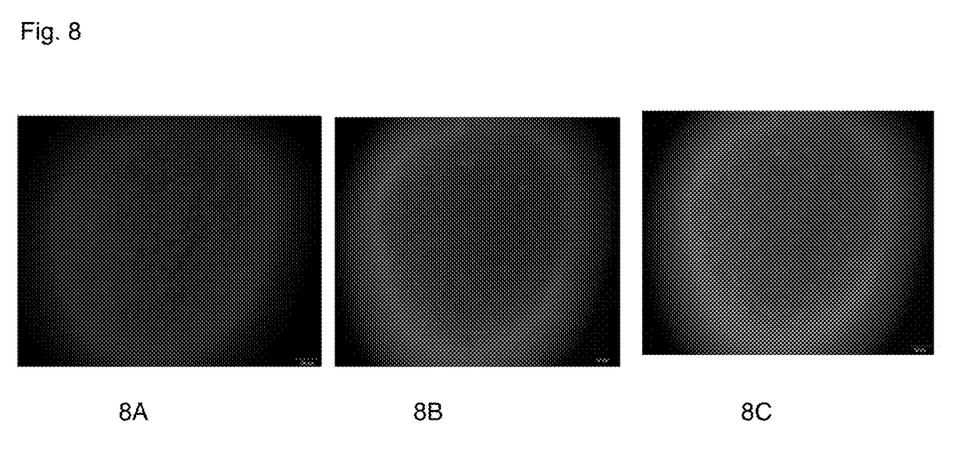
FIG. 8 shows analysis results at protein level of specific genes of insulin-secreting like cells obtained by inducing umbilical cord mesenchymal stem cells with the medium of the present invention, in which panel 8A shows staining result of nuclear protein PDX-1, panel 8B shows staining result of cytosol protein Insulin, and panel 8C shows a merge of panels 8A and 8B.

Results: insulin-secreting like cells were obtained by inducing with the method of the present invention which expressed INSULIN and PDX-1 specific proteins. The results are shown in FIG. 8.

Example 10: Measurement of Amount of Insulin Released Per Cell

After differentiation induction for 6 days, cell clusters in Example 6 were collected in a centrifuge tube, centrifuged and the supernatant was discarded. The cell clusters were resuspended in PBS, aspirated gently, and then centrifuged at 500 rpm for 3 minutes; the PBS was discarded and a stimulating liquid, DMEM with 5.5 mM/L glucose (group of low glucose) or DMEM with 25 mM/L glucose (group of high glucose) was added into the tube respectively. Afterwards, the cell clusters were blown gently and mixed well, and stimulated for 2 hours at 37° C., 5% $CO_2$. The tube was centrifuged at 500 rpm for 3 minutes, and the supernatant was collected for detection. The amount of insulin released was measured by ELISA, and a group of insulinoma cells was served as a positive control group.

Figure 9:
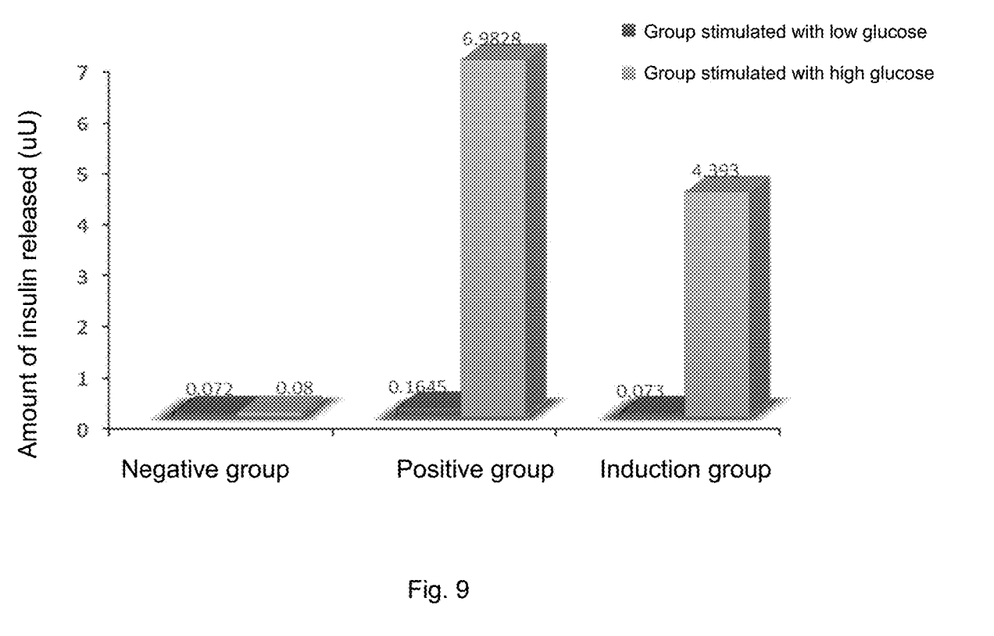
FIG. 9 shows the detection of the amounts of insulin released per $10^4$ insulin-secreting like cells after stimulating with low glucose and high glucose respectively, in which the insulin-secreting like cells are obtained by inducing umbilical cord mesenchymal stem cells with the medium of the present invention.

Results: insulin-secreting like cells were obtained by inducing with the method of the present invention which released 4.393 ulU/ml insulin per $10^4$ cells under stimulation of high glucose, and the cells of the positive control group released 6.9828 ulU/ml insulin per $10^4$ cells under stimulation of high glucose. That is, the amount of insulin released by the cells of induction group equals to 62.91% of the positive group. The results are shown in FIG. 9.

The above description for the embodiments of the present invention is not intended to limit the present invention, and those skilled in the art can make various changes and variations according to the present invention, which are within the protection scope of the present invention without departing from the spirit of the same.

What is claimed is:

1. A serum-free medium for inducing umbilical cord mesenchymal stem cells to differentiate into insulin-secreting like cells,
    wherein in 100 parts by volume, the serum-free medium consists of 85-95 parts by volume of DMEM (High Glucose, with 4.5 g/L glucose), 5-8 parts by volume of serum replacement, 1-4 parts by volume of B27 serum-free supplement (50×), 1-1.5 parts by volume of insulin-transferrin-selenium, 0.5-2 parts by volume of aqueous solution of non-essential amino acids, 0.5-2 parts by volume of N-2 serum-free supplement (100×), and heparin in a final concentration of 0.5-2 ug/ml, conophylline in a final concentration of 50-200 ng/ml, nicotinamide in a final concentration of 5-20 mmol/L, and recombinant human basic fibroblast growth factor, epidermal growth factor, hepatocyte growth factor and pentagastrin, each in a final concentration of 5-20 ng/ml; and
    wherein the aqueous solution of non-essential amino acids comprises glycine, alanine, L-asparagine, L-aspartic acid, glutamic acid, proline and serine, each in a concentration of 8-12 mM, and
    wherein the serum-free medium induces differentiation of a maximum number of insulin-secreting like cell clusters from the umbilical cord mesenchymal stem cells at 6 days.

2. The serum-free medium according to claim 1, wherein in 100 parts by volume, the serum-free medium consists of 89 parts by volume of DMEM (High Glucose, with 4.5 g/L glucose), 5 parts by volume of serum replacement, 2 parts by volume of B27 serum-free supplement (50×), 1 part by volume of insulin-transferrin-selenium (ITS), 1 part by volume of aqueous solution of non-essential amino acids, 1 part by volume of N-2 serum-free supplement (100×), and heparin in a final concentration of 1 µg/ml, conophylline in a final concentration of 100 ng/ml, nicotinamide in a final concentration of 10 mmol/L, and recombinant human basic fibroblast growth factor, epidermal growth factor, hepatocyte growth factor and pentagastrin each in a final concentration of 10 ng/ml.

3. The serum-free medium according to claim 1, wherein the umbilical cord mesenchymal stem cells are umbilical cord mesenchymal stem cells of human origin.

4. A method for preparing the serum-free medium according to claim 1, the method including: mixing medium ingredients until evenly dispersed.

5. A method for inducing umbilical cord mesenchymal stem cells to differentiate into insulin-secreting like cells, the method including: culturing the umbilical cord mesenchymal stem cells with the serum-free medium according to claim 1.

6. The method according to claim 5, wherein the umbilical cord mesenchymal stem cells are umbilical cord mesenchymal stem cells of human origin.

7. IThe method according to claim 5, wherein the method includes the following steps:
    (1) inoculating umbilical cord mesenchymal stem cells in the serum-free medium in a ultra-low attachment six well plate at a density of 5×104 cells/cm² and culturing the cells at 37° C., 5% $CO_2$;
    (2) every 2 days, centrifuging the cell culture of step (1) at 500 rpm for 4 min, removing the medium, and replacing with a fresh batch of the serum-free medium;
    (3) culturing for 6-7 days, and harvesting cells; and
    (4) detecting the cells harvested in step (3) for effect of differentiation induction.

8. The method according to claim 5, wherein the umbilical cord mesenchymal stem cells are human umbilical cord mesenchymal stem cells isolated from a fresh umbilical cord tissue of a healthy newborn delivered naturally or by cesarean section.

9. The method according to claim 5, wherein the method includes the following steps:
    (1) inoculating umbilical cord mesenchymal stem cells in the serum-free medium at a density of 2-6×104 cells/cm² and culturing the cells at 37° C., 5% $CO_2$;
    (2) every 2-3 days, centrifuging the cell culture of step (1) at 300-800 rom for 4 min, removing the medium, and replacing with a fresh batch of the serum-free medium;
    (3) culturing for 6-7 days, and harvesting cells; and
    (4) detecting the cells harvested in step (3) for effect of differentiation induction.

10. The method according to claim 9, wherein the step (4) comprises detecting one or more items selected from the group consisting of: amount of insulin released per cell; expression of insulin release-related genes PDX-1, INSULIN and NGN-3; presence of cell nuclear protein PDX-1 and cytosol protein Insulin; dithizone staining; and positive expression rates of specific markers PDX-1, NKX6.1 and insulin of insulin-secreting like cells.

11. The serum-free medium according to claim 1, wherein the umbilical cord mesenchymal stem cells are human umbilical cord mesenchymal stem cells isolated from a fresh umbilical cord tissue of a healthy newborn delivered naturally or by cesarean section.

\* \* \* \* \*